United States Patent
Laugere et al.

(10) Patent No.: US 9,945,519 B2
(45) Date of Patent: Apr. 17, 2018

(54) DISPENSE INTERFACE

(71) Applicant: Sanofi-Aventis Deutschland GmbH, Frankfurt am Main (DE)

(72) Inventors: Frederic Laugere, Bedfordshire (GB); Cristian Popa, Norfolk (GB); Ben Impey, Cambridgeshire (GB); Andrew L. MacLeod, Cambridgeshire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 682 days.

(21) Appl. No.: 14/400,296

(22) PCT Filed: May 16, 2013

(86) PCT No.: PCT/EP2013/060165
§ 371 (c)(1),
(2) Date: Nov. 10, 2014

(87) PCT Pub. No.: WO2013/171312
PCT Pub. Date: Nov. 21, 2013

(65) Prior Publication Data
US 2015/0096623 A1  Apr. 9, 2015

(30) Foreign Application Priority Data

May 16, 2012 (EP) .................................... 12168375

(51) Int. Cl.
*F17D 1/08* (2006.01)
*A61M 5/19* (2006.01)
(Continued)

(52) U.S. Cl.
CPC ................. *F17D 1/08* (2013.01); *A61M 5/19* (2013.01); *A61M 5/2448* (2013.01);
(Continued)

(58) Field of Classification Search
CPC ...... A61M 5/19; A61M 5/2448; A61M 5/284; A61M 5/31596; F17D 1/08
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 1064622 A | 9/1992 |
| CN | 1402645 A | 3/2003 |

(Continued)

OTHER PUBLICATIONS

English Translation of Search Report Issued in Chinese Patent Application No. 201380023527X dated Jul. 13, 2016.

*Primary Examiner* — Theodore Stigell
(74) *Attorney, Agent, or Firm* — McDonnell Boehnen Hulbert & Berghoff LLP

(57) ABSTRACT

The present patent application relates to a dispense interface comprising a channel profile with at least two inlet channels and at least one outlet channel, wherein each of the at least two inlet channels is configured for fluid communication with a respective reservoir of at least two reservoirs, at least one top layer and one bottom layer, an intermediate layer structure arranged between the at least one top layer and one bottom layer, wherein intermediate layer structure is tightly laminated with the top layer and the bottom layer and wherein the intermediate layer structure comprises at least one intermediate layer comprising at least one recess for forming at least one part of the channel profile.

12 Claims, 12 Drawing Sheets

(51) Int. Cl.
  *A61M 5/24* (2006.01)
  *A61M 5/28* (2006.01)
  *A61M 5/315* (2006.01)

(52) U.S. Cl.
  CPC ......... *A61M 5/284* (2013.01); *A61M 5/31596* (2013.01); *Y10T 137/0318* (2015.04); *Y10T 137/87676* (2015.04)

(56) References Cited

U.S. PATENT DOCUMENTS

| | | |
|---|---|---|
| 5,279,586 A | 1/1994 | Balkwill |
| 5,286,258 A | 2/1994 | Haber et al. |
| 5,304,152 A | 4/1994 | Sams |
| 5,320,609 A | 6/1994 | Haber et al. |
| 5,383,865 A | 1/1995 | Michel |
| 5,478,323 A | 12/1995 | Westwood et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0265570 A1 | 11/2007 | Gerut |
| 2009/0275916 A1 | 11/2009 | Harms et al. |

FOREIGN PATENT DOCUMENTS

| | | | |
|---|---|---|---|
| EP | 0937471 A2 | 8/1999 | |
| EP | 0937476 A2 | 8/1999 | |
| WO | 9416348 A1 | 7/1994 | |
| WO | 9422507 A2 | 10/1994 | |
| WO | WO 9426348 A1 * | 11/1994 | ............ A61M 5/152 |
| WO | 9938554 A1 | 8/1999 | |
| WO | 0110484 A1 | 2/2001 | |
| WO | 0132235 A2 | 5/2001 | |
| WO | 2011117404 A2 | 9/2011 | |

* cited by examiner

DISPENSE INTERFACE

CROSS REFERENCE TO RELATED APPLICATIONS

The present application is a U.S. National Phase Application pursuant to 35 U.S.C. § 371 of International Application No. PCT/EP2013/060165 filed May 16, 2013, which claims priority to European Patent Application No. 12168375.9 filed May 16, 2012. The entire disclosure contents of these applications are herewith incorporated by reference into the present application.

FIELD OF INVENTION

The present patent application relates to an ejection device, for example a medical device, for delivering at least two liquids, such as liquid drug agents, from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

SUMMARY

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The dispense interfaces in the state of the art are, however, often of complex design. In order to provide the manifold to lead the medicaments from two different reservoirs to a single outlet, multiple complex and/or small parts need to be produced and assembled. In particular, small parts having a complex shape must be molded with a high accuracy.

Besides the need of complex and special cavities for forming the respective parts, the assembly of the molded parts and the integration of the needles can be complex as well. The complex part structures and the corresponding complicated assembly steps may cause the dispense interface to be difficult to manufacture and expensive.

Additionally, the dispense interface is regularly kept at the drug delivery device for a longer period of time. This means that only the dose dispenser in form of a double ended needle, for instance, is exchanged for every or nearly every injection procedure. The dispense interface, however, remains at the drug delivery device. An exchange of the dispense interface itself is regularly only necessary, when the reservoirs of the drug delivery device need to be exchanged.

This causes requirements for the material and design of the dispense interface to be fulfilled. Since the drug agents from the first and/or the second reservoir remain inside the dispense interface after a dispense procedure, a material compatibility of the parts of the dispense interface being in contact with the drug agents needs be to provided. No harmful substances must diffuse into the drug agents, since these would then be delivered to the patient with the next delivery procedure. Hence a biocompatibility is required, which guarantees that either no or negligible amounts of substances can diffuse into drug agents or are set free into the liquid.

Furthermore, if the dispense interface remains attached to the drug delivery device the different drug agents also start to diffuse into each other over time. A cross-contamination of the drug agents from one reservoir into the other reservoir needs to be prevented for the above mentioned reasons of stability, compromised therapeutic performance and toxicology, for example.

In order to prevent such cross-contamination, non-return valves can be implemented in the dispense interface. This, however, increases the part count and thus the complexity and cost during the production of the dispense interface. Additionally, a septum is often provided at the outlet of the dispense interface, since the dispense interface needs to be sealed, when it is connected to the reservoirs but there is no dose dispenser attached.

In light of the aforementioned, the invention faces the technical problem of reducing the complexity and providing an easy manufacture and usage of the dispense interface and at the same time overcoming the problems of material compatibility and cross contamination.

The technical problem is solved by a dispense interface comprising a channel profile with at least two inlet channels and at least one outlet channel, wherein each of the at least two inlet channels is configured for fluid communication with a respective reservoir of at least two reservoirs, at least one top layer and one bottom layer and an intermediate layer structure arranged between the at least one top layer and one bottom layer, wherein the intermediate layer structure is tightly laminated with the top layer and the bottom layer, wherein the intermediate layer structure comprises at least one intermediate layer comprising at least one recess for forming at least one part of the channel profile.

By providing a dispense interface having at least three laminated layers, wherein at least one intermediate layer comprises at least one recess for forming at least a part of the channel profile, the production and assembly of the dispense interface can be kept simply.

In particular, the stacking of at least three layers one above the other simplifies the production and assembly of the dispense interface, since it is not required to mold complex part structures. The stacked layers are tightly connected to each other to form a body comprising the channel profile. The channel profile can be produced by merely recessing at least one intermediate layer. For instance, by joining the bottom layer and the top layer to the intermediate layer comprising the recess, a fluidic channel can be established.

The cost efficient and easy production process allows the dispense interface to be replaced frequently, thus reducing the risk of contamination. In particular, it enables the dispense interface to be used as a single-use item. This means that after a single delivery procedure with an ejection of a liquid or a drug agent through the dispense interface the dispense interface can be detached from the ejection device and discarded.

The ejection device can, for instance, be a medical device such as a drug delivery device.

During an ejection procedure a liquid may enter the dispense interface through the first inlet channel and another liquid may enter the dispense interface through the second inlet channel which are a part of the channel profile. The liquids can leave the dispense interface via the outlet channel which is also a part of the channel profile. The dispense interface can be seen as a manifold.

Since the dispense interface is only in connection with the reservoirs of the ejection device substantially during the ejection procedure, there is only a short time for possible substances or chemicals in the dispense interface to diffuse into the liquid ejected by the ejection device and guided through the inlet and outlet channels.

There is also substantially no time for the liquids within the reservoirs to become cross-contaminated, since the dispense interface is directly detached after the ejection procedure as it can be thrown away.

Furthermore there is no need for a septum in the dispense interface, since an exchange of a third needle, like an ejection needle, is not necessary, since after each injection an exchange of the whole dispense interface can take place.

As a consequence of the above mentioned, the complexity of the dispense interface is reduced, an easy usage and manufacturing of the dispense interface is provided and at the same time the problems of material compatibility and cross-contamination are overcome.

According to an embodiment of the dispense interface of the invention, the intermediate layer structure comprises a first intermediate layer comprising at least one first recess for forming at least one part of the first inlet channel and one second recess for forming at least one part of the second inlet channel. The first intermediate layer may be a flat layer comprising a presettable thickness. Preferably, the shape of the first intermediate layer is similar to the shape of the bottom and/or top layer. By forming a first recess, for instance by cutting a first recess, at least one part of the first inlet channel can be formed. Preferably, the respective recess forms the respective inlet channel. For instance, a linear recess with a predetermined width and length can be formed. The height of the inlet channel can be identical with the thickness of the first intermediate layer. For increasing the height of an inlet channel, the thickness of the first intermediate layer can be increased and/or a plurality of substantially identical first layers can be stacked one above the other. The second recess can have the same shape as the first recess. In particular, the second recess can run in parallel with the first recess.

Preferably, the bottom layer and the first intermediate layer can be tightly laminated to each other. For instance, the at least two layers are tightly laminated to each other by bonding techniques and/or welding techniques. The first recess can be the first inlet channel and the second recess can be the second inlet channel. The bottom layer may provide the bottom wall of the at least first and second inlet channels. The top wall of the respective channels can be provided by e.g. a further intermediate layer. The side walls if the respective channels can be provided by the first intermediate layer. The first and second inlet channel can be manufactured in a particular simple and cost-efficient way.

Furthermore, according to another embodiment of the dispense interface of the invention, the intermediate layer structure comprises a second intermediate layer comprising at least one first recess for forming at least one part of the outlet channel. In particular, the respective recess is the outlet channel. The second intermediate layer may be a flat layer comprising a presettable thickness. Preferably, the shape of the second intermediate layer is similar to the shape of the bottom and/or top layer. By forming a first recess, for instance by cutting a first recess, at least one part of the outlet channel can be formed. For instance, a linear recess with a predetermined width and length can be formed. The height of the outlet channel can be identical with the thickness of the second intermediate layer. For increasing the height of the channel, the thickness of the second intermediate layer can be increased and/or a plurality of substantially identical second layers can be stacked one above the other.

In another embodiment of the dispense interface according to the invention, the second intermediate layer comprises at least one second recess for forming at least one part of a central space configured for fluid connection between the outlet channel and the first inlet channel and the second inlet channel. In particular, the second recess is the central space. The second recess may be arranged at one end of the first recess of the second intermediate layer. For instance, the first and second recess may have a T shaped form.

Preferably, the top layer and the second intermediate layer can be tightly laminated to each other. For instance, the at least two layers are tightly laminated to each other by bonding techniques and/or welding techniques. The bottom layer may provide the top wall of the at least one outlet channel and/or the central space. The bottom wall of the outlet channel and/or central space can be provided by e.g. a further intermediate layer. The side walls of the respective channel and space can be provided by the second intermediate layer.

In addition, according to another embodiment of the dispense interface according to the invention, the intermediate layer structure comprises a third intermediate layer comprising at least a first opening configured for fluid connection between the first inlet channel and the central space and a second opening configured for fluid connection between the second inlet channel and the central space. An opening, like a circular recess, rectangular recess, triangular recess or elliptical recess, may be formed by e.g. cutting. Both openings may be preferably of the same shape. The openings may have a distance to each other similar to the distance between the first and second inlet channels. Furthermore, the openings may be arranged in such a way that in case the third intermediate layer is arranged above the first intermediate layer, the openings are above the respective endings of the two inlet channels. A fluid connection between the inlet channels and the outlet channels via the central space can be provided.

Preferably, the third intermediate layer and the first intermediate layer can be tightly laminated to each other. For instance, the at least two layers are tightly laminated to each other by bonding techniques and/or welding techniques. The intermediate layer may provide the top wall of the at least first inlet channel and second inlet channel. The bottom wall of the first inlet channel and second inlet channel can be provided by e.g. the bottom layer.

Alternatively or additionally, the third intermediate layer and the second intermediate layer can be tightly laminated to each other. For instance, the at least two layers are tightly laminated to each other by bonding techniques and/or welding techniques. The intermediate layer may provide the top wall of the at least one outlet channel and the central space. The top wall of the at least one outlet channel and the central space can be provided by e.g. the top layer. A simple and cost-efficient producible dispense interface having a desired channel profile can be provided.

It shall be understood that the intermediate layer structure may comprise further intermediate layers.

It may be advantageous if a fluid flow from the outlet channel to the inlet channel is prohibited. Preferably, also a fluid flow from one inlet channel to the other inlet channel should be prevented. Therefore, a valve mechanism can be integrated in the dispense interface. According to an embodiment of the dispense interface of the invention, the at least two openings of the third intermediate layer are provided with a non-return valve mechanism. The non-return valve mechanism may be configured to enable a fluid flow in only one direction.

Generally, the non-return valve mechanism can be arbitrarily designed. In a preferred embodiment of the dispense interface according to the invention, the non-return valve mechanism is formed by a laser cut polymer film. By cutting a thin polymer film such that two movable flaps are generated, the valve mechanism can be manufactured in a simple way. A flap may be configured to allow a fluid flow only in one direction. For instance, if a pressure is exerted onto the flap from the inlet channel, the flap is opened. In case, a pressure is exerted onto the flap from the other direction, the flap is kept closed.

Furthermore, a layer, like a top layer, bottom layer and/or intermediate layer can be made of any material suitable for the use with the fluid to be dispensed. According to one embodiment of the dispense interface according to the invention, at least one of the plurality of layers is made of a polymer material. Preferably, all layers of the laminated dispense interface are made of a polymer material, in particular, the same polymer material. Besides the low cost of a polymer layer, such a layer can be easily processed. For instance, cutting a recess and/or tightly laminating two polymer layers to each other can be performed with low efforts and cost.

In a further embodiment of the dispense interface according to the invention, each of the at least two inlet channels comprises an inlet opening, wherein the at least one outlet channel comprises an outlet opening and wherein at least one of the inlet or outlet openings is provided with a needle. Preferably, a first and second proximal needle and an ejection needle can be integrated in the dispense interface. For instance, before laminating the respective layers to each other, the respective needles can be inserted. The layers can then be laminated together with the needles resulting in a compact dispense interface comprising at least one, preferably the first and second proximal needle and the ejection needle.

Alternatively, separate needle assemblies connectable to the dispense interface can be provided.

Since a user can be injured by a needle if the dispense assembly is used carelessly, the at least one needle, preferably all needles, can be covered by a safety element. According to an embodiment of the dispense interface of the invention, at least one needle is covered by at least one safety element, wherein the at least one safety element is formed by an extension of at least one layer of the plurality of layers. The at least one safety element, e.g. a needle cover, can be an integral part of dispense interface. At least one layer can be enlarged for covering at least the needle tip. A compact dispense interface without additional and separate parts, like separate needle covers, can be provided.

Alternatively, the at least one safety element may be a cap or the like.

To enable a simple detachment of the at least one safety element, a predetermined breaking line configured for removing the at least one safety element from the at least one needle is arranged. For instance, a perforated line can be provided which enables that the safety element can be correctly and easily detached from the dispense interface.

The technical problem is further solved by a method for manufacturing a dispense interface comprising the steps of providing at least one bottom layer and one top layer, providing an intermediate layer structure comprising at least one intermediate layer, recessing at least the at least one intermediate layer for forming at least one part of a channel profile and tightly laminating the top layer and the bottom layer to the intermediate layer structure.

A dispense interface, in particular a previously described dispense interface, can be manufactured easily, if a plurality of layers are stacked one above the other, wherein at least one recess is formed into at least one intermediate layer. It is not required to mold complex part structures and to assemble the respective parts. Preferably, the channel structure can be formed by forming a recess in an intermediate layer and tightly laminating a bottom layer and a top layer to the intermediate layer.

The technical problem is further solved by a system comprising a previously described dispense interface and an ejection device, wherein the dispense interface is attached to the ejection interface.

The user can attach the dispense interface directly before an ejection procedure. For this purpose, connection elements may be provided. Preferably, the needles are already integrated in the dispense interface. Further steps, like attaching a first needle assembly and attaching a second needle assembly can be omitted. The dispense interface can be exchanged more frequently, or even after every use.

As a consequence, the complexity of the dispense interface can be reduced, an easy usage of the dispense interface can be provided and at the same time the problems of material compatibility and cross contamination are overcome.

According to an embodiment of the system according to the invention, the ejection device is a medical device for delivering at least two drug agents from at least two separate reservoirs.

The technical problem is further solved by a method for using the previously described system comprising attaching the dispense interface to an ejection device having at least two reservoirs such that a fluid tight connection is established between said at least two reservoirs and the dispense interface, ejecting a fluid from at least one of the reservoirs out of the dispense interface, and detaching the dispense interface from the ejection device.

Preferably, the dispense interface comprises at least first and second proximal needles resulting in a compact dispense interface since the needles are integrated in the dispense interface. Furthermore, the dispense interface can be easily attached to the ejection device. Further steps for attaching a separate needle assembly can be omitted. Preferably, the user attaches the dispense interface to the ejection device after taking the dispense interface out of a packaging. It is in particular possible and still economical for the user, to exchange the dispense interface more frequently, or even after every use. In other variants, a separate needle assembly may be attached to the dispense interface.

Since the needles are integrated in the dispense interface, an easy usage of the dispense interface is provided. At the same time the problems of material compatibility and cross contamination are overcome, since the user establishes the connection of the dispense interface with the reservoirs directly before an ejection and the user can remove it directly afterwards as well.

When the user attaches the dispense interface to the ejection device, preferably the first proximal needle provides a fluid tight connection to the first reservoir of the ejection device, for example by piercing a septum of the first reservoir, while the second proximal needle provides a fluid tight connection to the second reservoir of the ejection device, for example by piercing a septum of the second reservoir.

The dispense interface may be secured in an engaged position with the ejection device. This can be done by fixing elements provided by the ejection device, for example. Such fixing elements, hooks or protrusions adapted to the dispense interface for instance, may establish a positive fit between the dispense interface and the ejection device. Alternatively, it is also possible that the dispense interface is fixed in the engaged position with the ejection device only by friction fit.

In case the needle tips of the first and second needle assemblies are covered with safety elements, e.g. needle covers, the user needs to remove these covers before attaching the dispense interface to the ejection device. In case the needle tip of the third needle is covered with a safety element, like a needle cover, the user needs to remove this cover before performing an ejection procedure. If the cover is formed by an extension of at least one layer and if the extension is provided by a predetermined breaking line, the respective needle cover can be removed easily from the respective needle.

Preferably, the method according to the invention further comprises the steps of ejecting a fluid from at least one of the reservoirs through the dispense interface and then removing the dispense interface form the ejection device.

These steps are performed after having attached the dispense interface to the injection device. When the dispense interface is removed after an ejection procedure, for example by the user, the risk of possible contaminations of the fluids and/or the reservoirs is reduced. Preferably, the dispense interface is removed directly after an ejection procedure. The dispense interface can then be discarded with the (integrated) needles.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
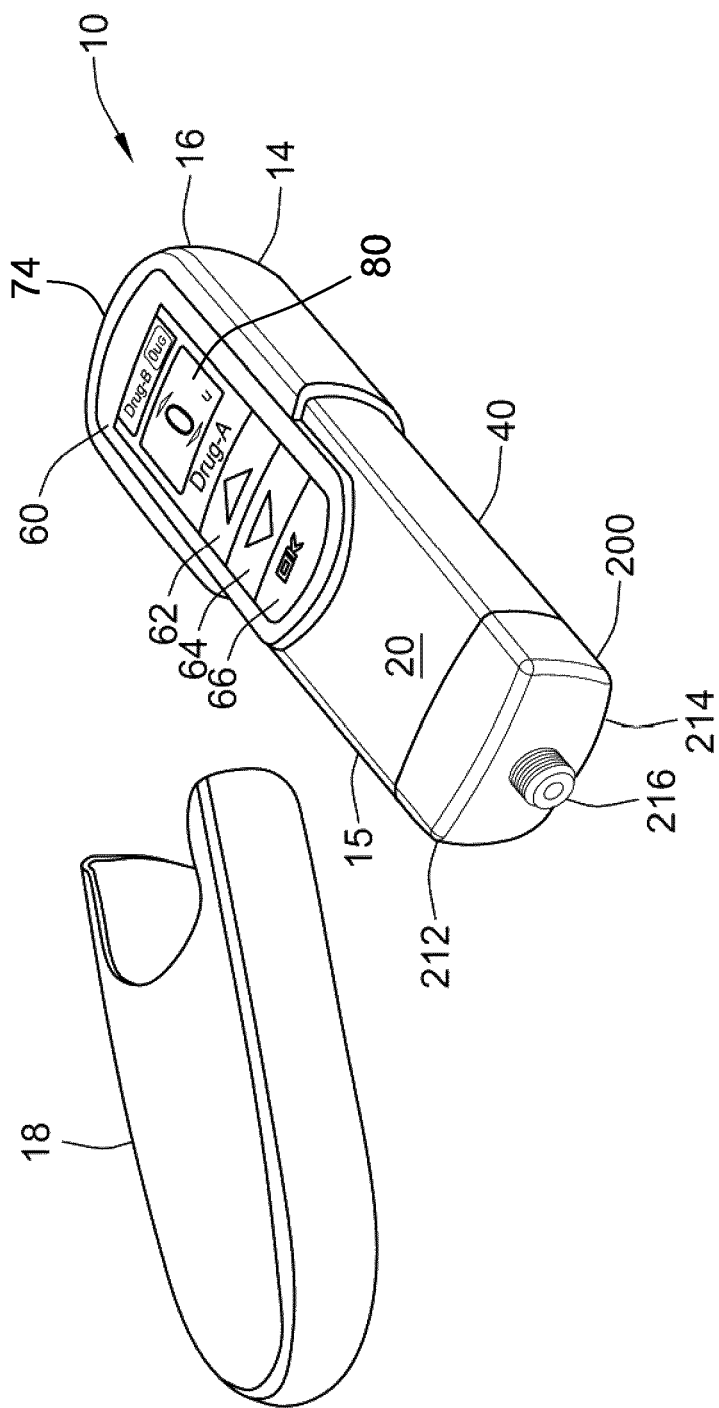
FIG. 1 illustrates a perspective view of a delivery device with an end cap of the device removed.
Figure 2:
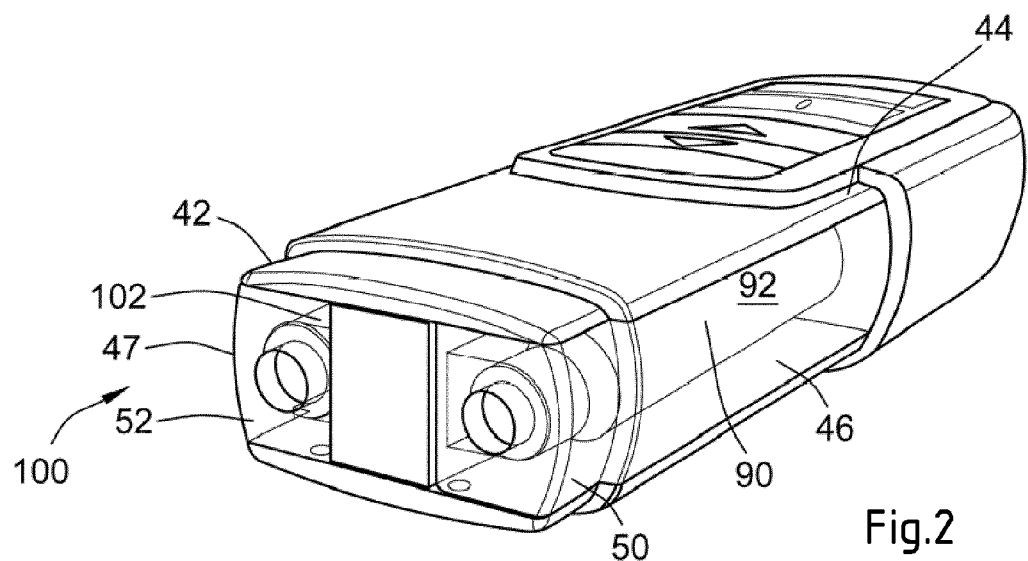
FIG. 2 illustrates a perspective view of the delivery device distal end showing the cartridge.

The ejection device in the form of a drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 210 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
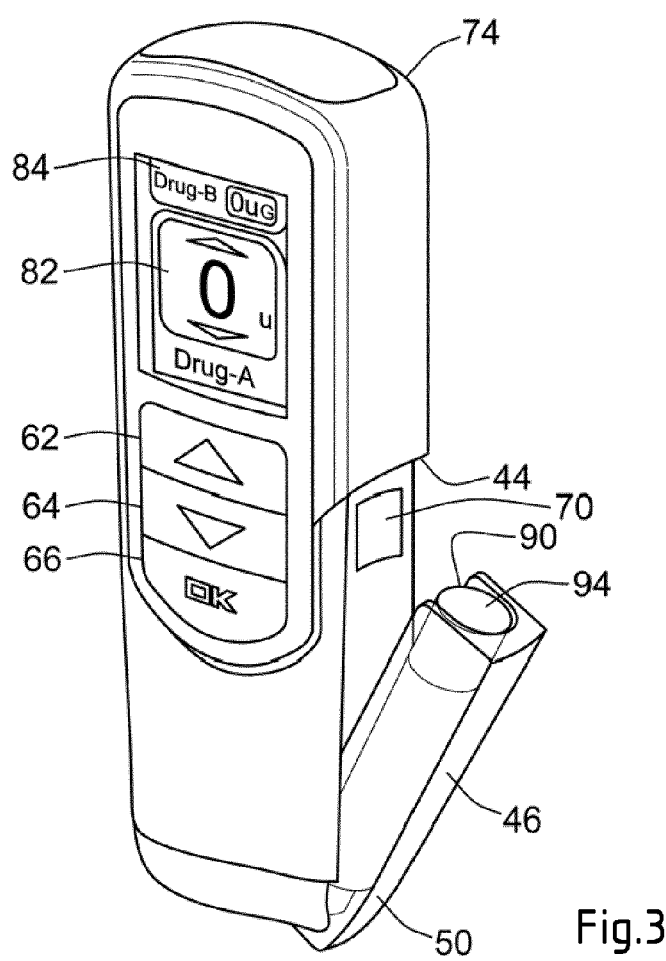
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
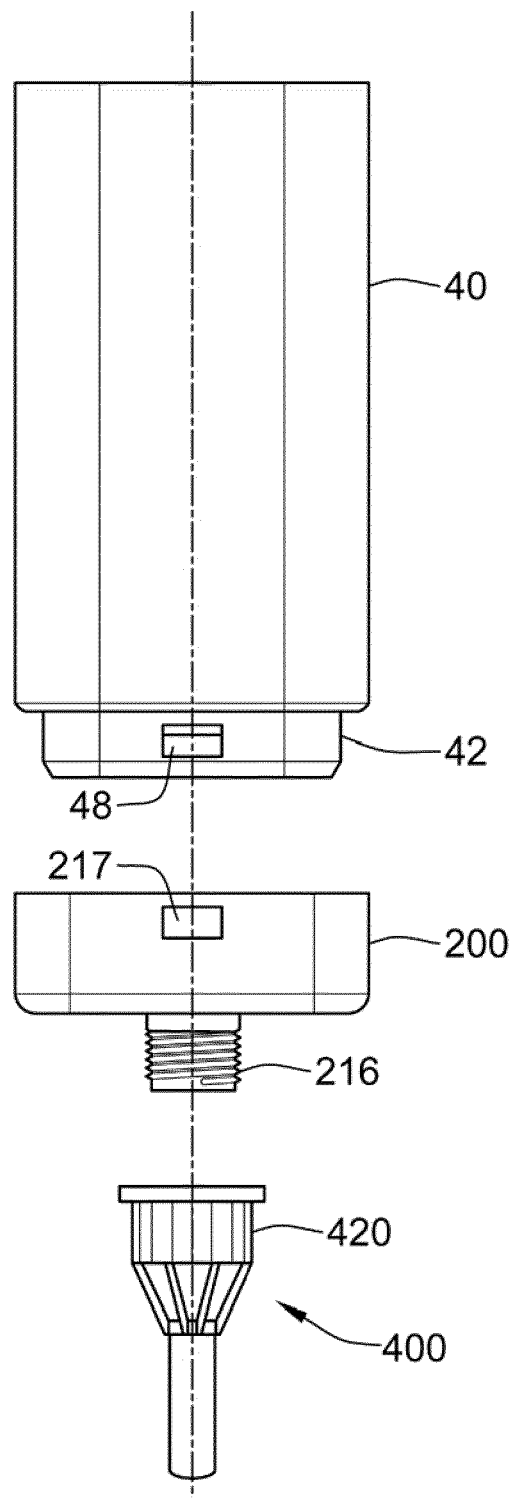
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
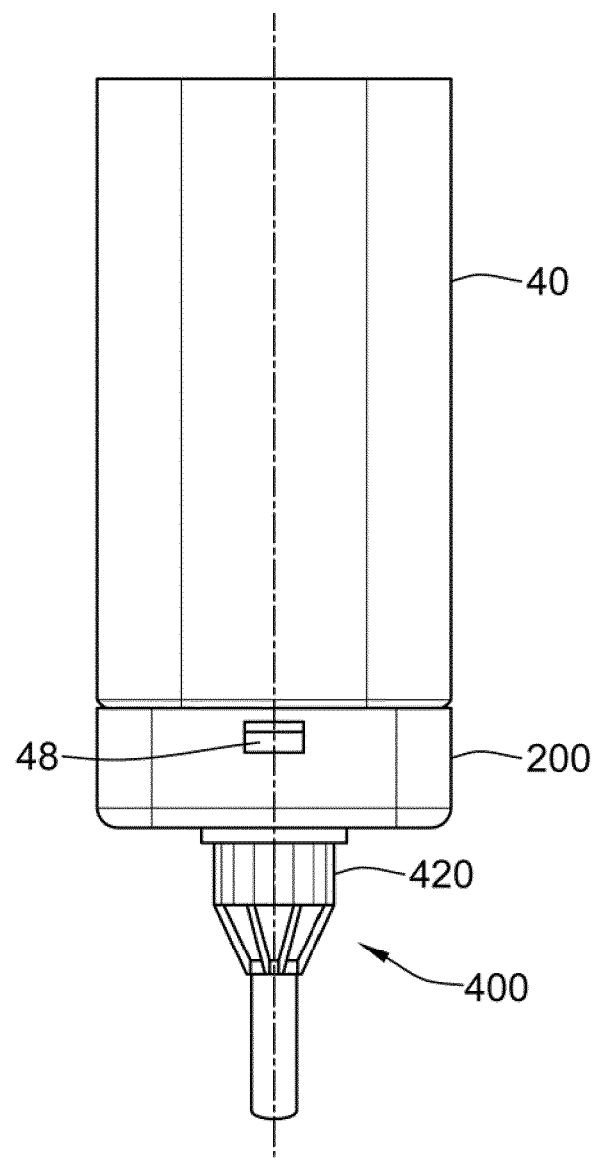
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
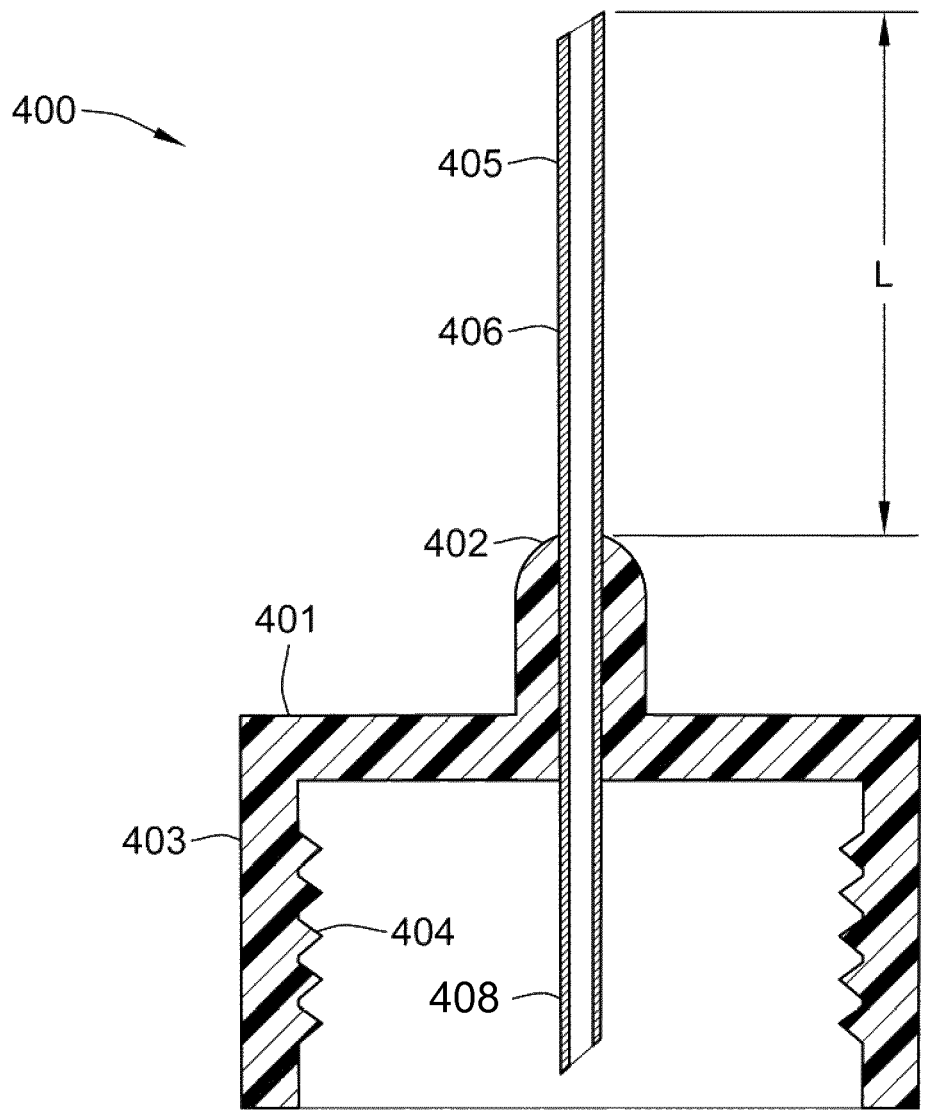
FIG. 6 illustrates one arrangement of a needle assembly that may be mounted on a distal end of the delivery device.
Figure 7:
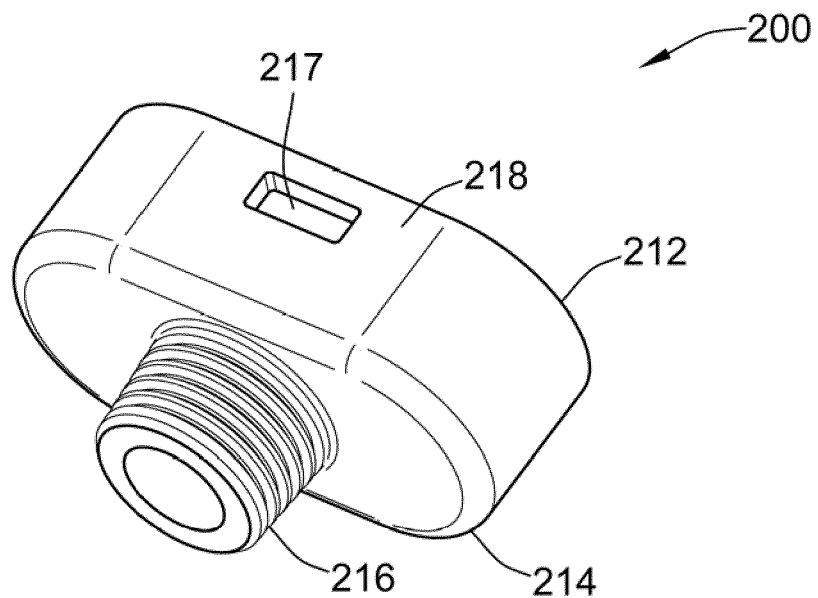
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
 a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
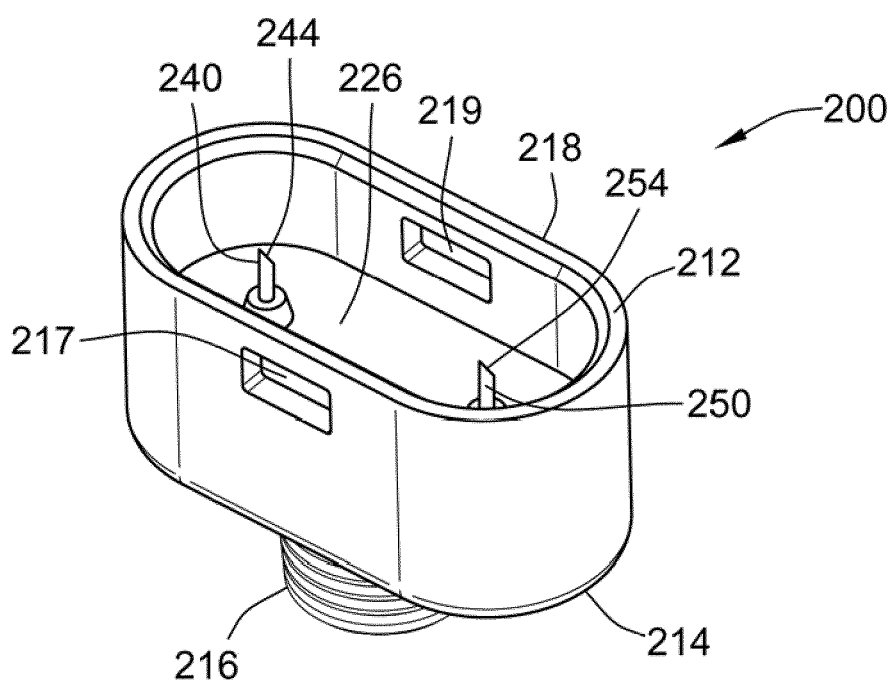
FIG. 8 illustrates another perspective view of the dispense interface illustrated in FIG. 4.
Figure 9:
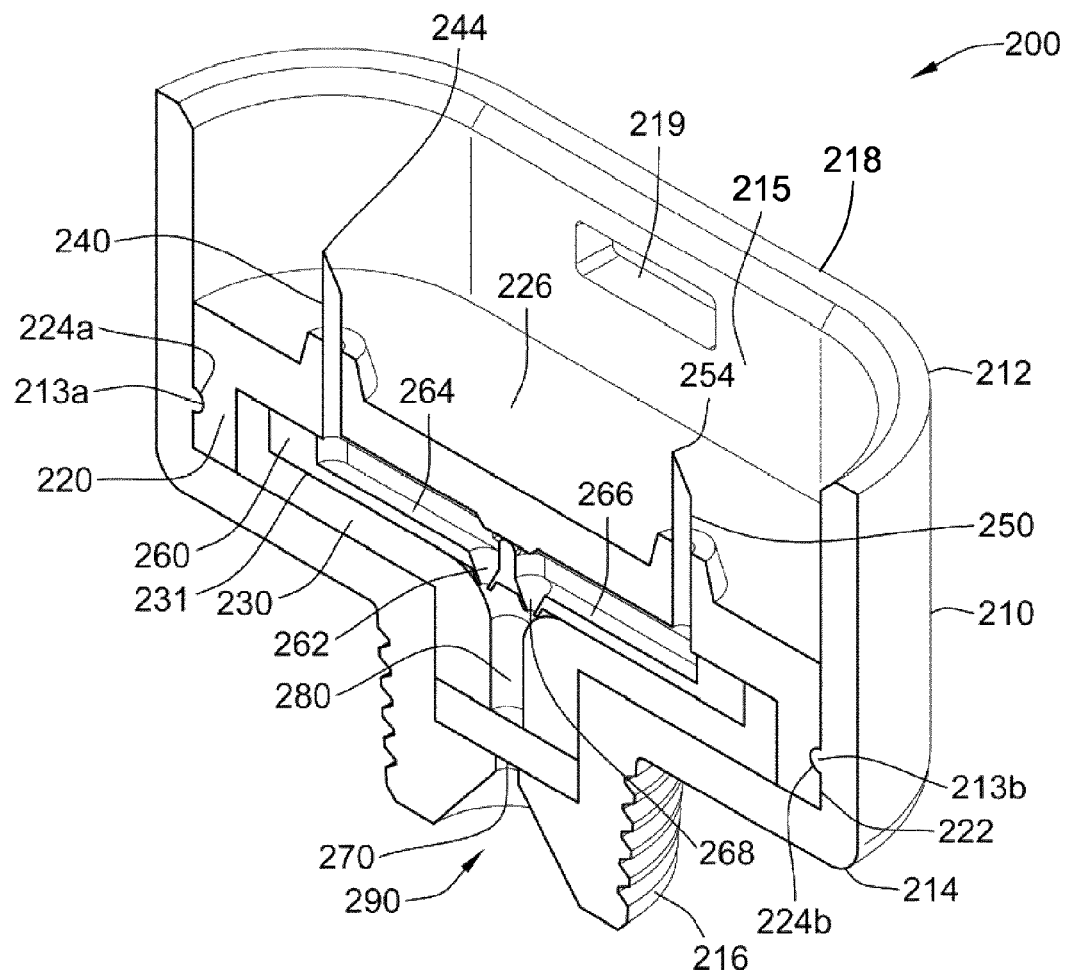
FIG. 9 illustrates a cross-sectional view of the dispense interface illustrated in FIG. 4.
Figure 10:
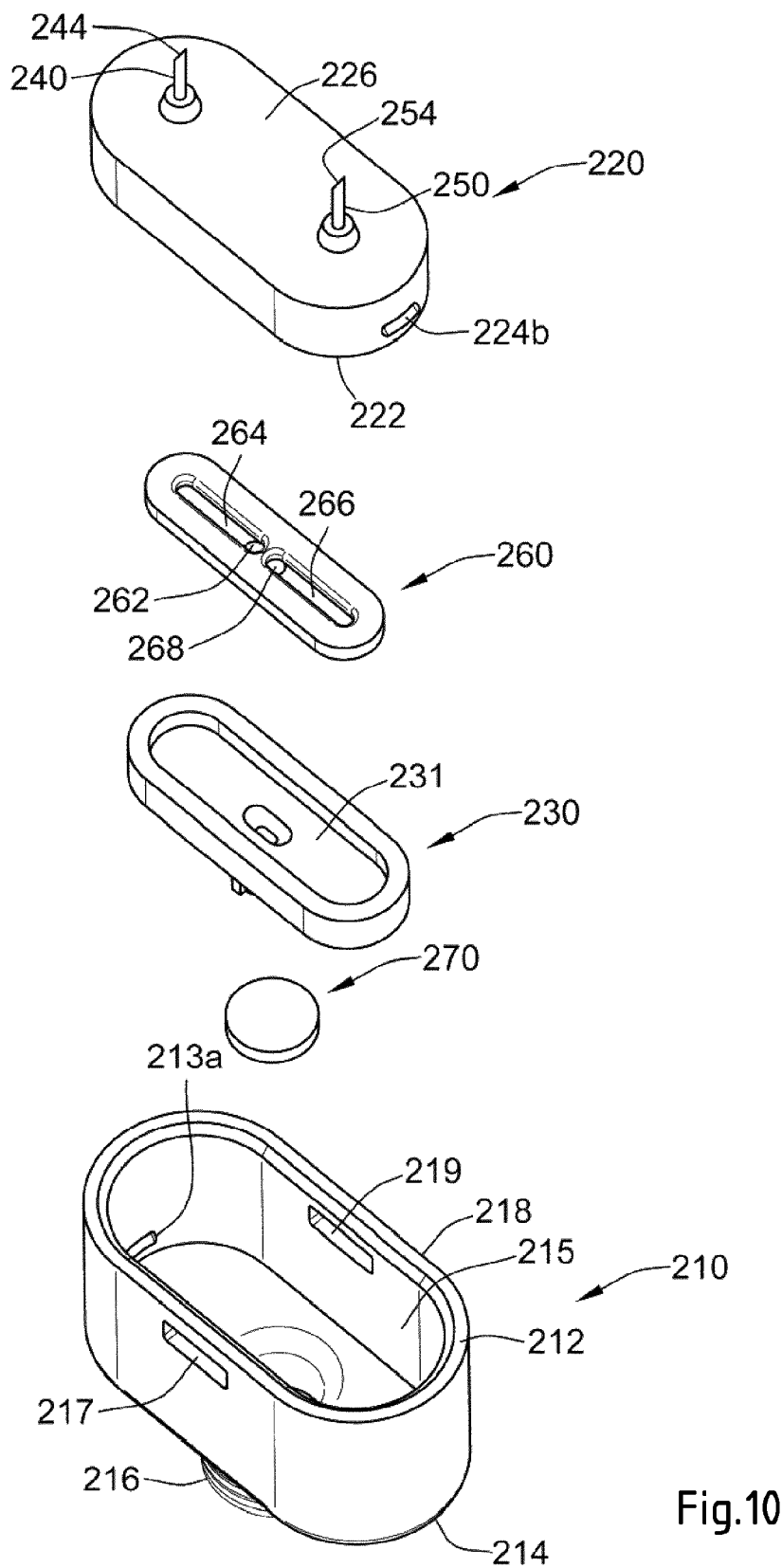
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are sealingly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
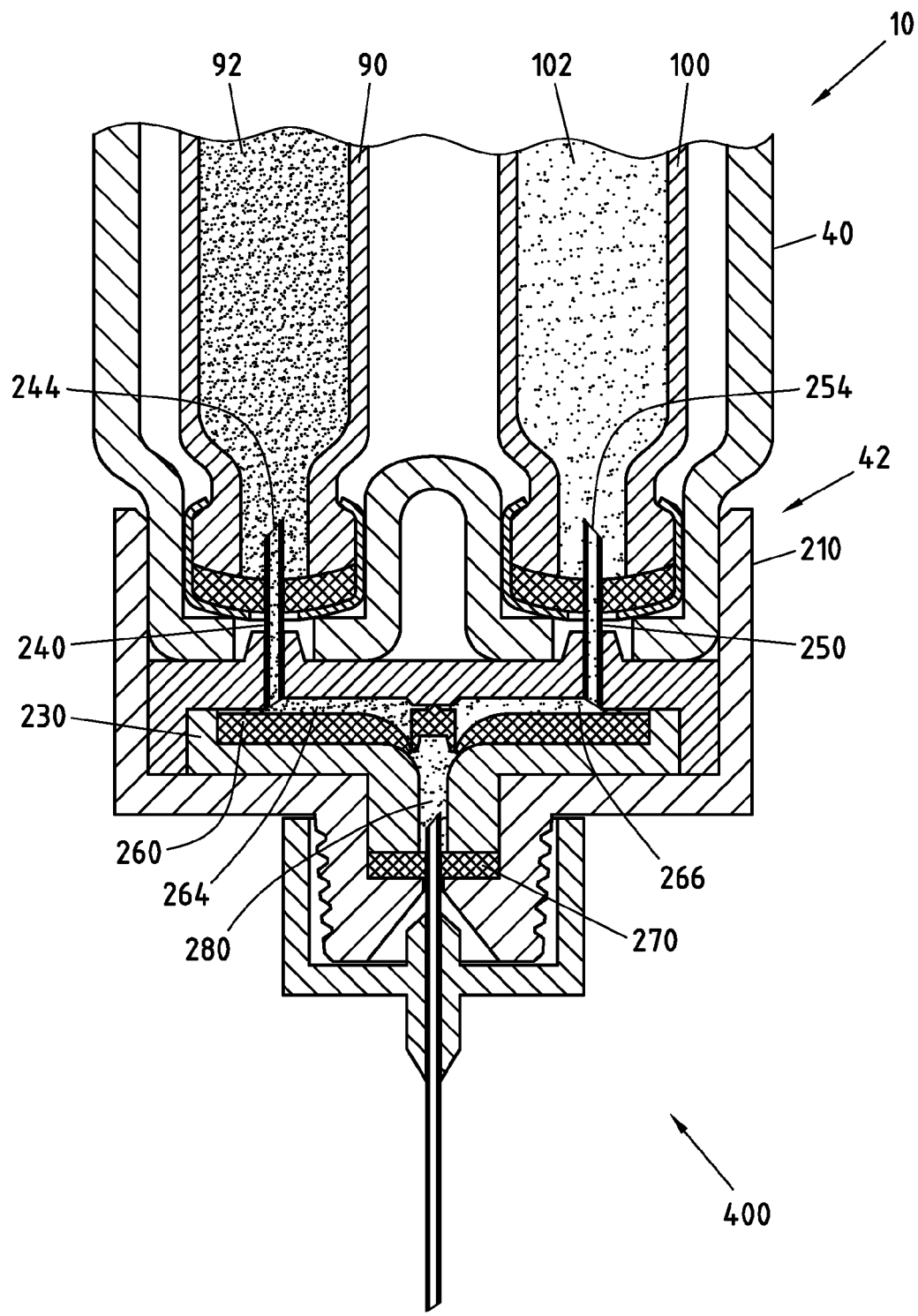
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
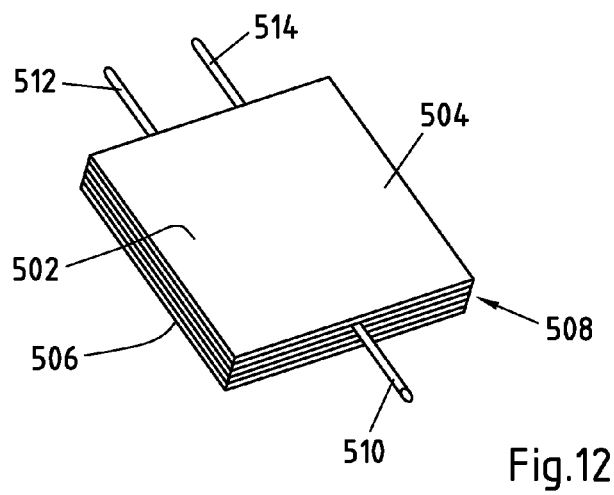
FIG. 12 illustrates a perspective view of a dispense interface according to the invention.

FIG. 12 illustrates a perspective view of a dispense interface 500 according to the invention.

The illustrated dispense interface 500 comprises a top layer 502, a bottom layer 506 and an intermediate layer structure 508. The top layer 502, the bottom layer 506 and the intermediate layer structure 508 form a body 504.

As can be seen from FIG. 12, the intermediate layer structure 508 comprises a plurality of intermediate layers. The top layer 502, the plurality of intermediate layers of the intermediate layer structure 508 and the bottom layer 506 are stacked one above the other. Two adjacent layers can be tightly laminated to each other. For instance, two adjacent layers can be bonded and/or welded together.

Each layer may be made of a polymer material. For instance, a suitable plastic material can be used.

Furthermore, the dispense interface 500 comprises a first and a second proximal needle 512 and 514. The first and second proximal needle 512 and 514 can pierce a first reservoir containing a primary compound and a second reservoir containing a secondary compound, respectively. The first and a second proximal needle 512 and 514 can be tightly integrated in the dispense interface 500.

The dispense interface 500 comprises further a third needle 510, e.g. an ejection needle 510. The third needle 510 can be tightly integrated in the dispense interface 500.

The dispense interface 500 in the present example has a rectangular shape. It shall be understood that according to other variants of the invention, the shape may be different and for instance adapted to the shape and/or design of the ejection device. Since preferably a polymer material is used, the respective layers can be easily formed to obtain a desired shape.

Figure 13:
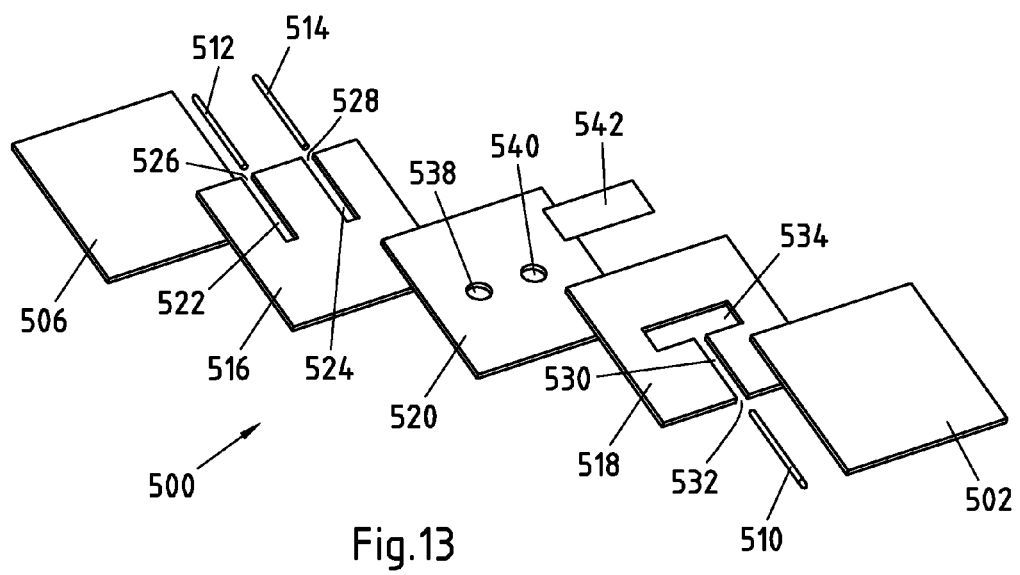
FIG. 13 illustrates a perspective view of the dispense interface of FIG. 12 with multiple layers not joined to each other.

FIG. 13 illustrates a perspective view of the dispense interface 500 of FIG. 12 with multiple layers 502, 506, 516, 518, 520 not joined to each other.

The illustrated bottom layer 506 of the dispense interface 500 is a flat and even layer 506 without any openings or recesses. In the present example, the bottom layer 506 has a rectangular shape. It shall be understood that, according to other variants of the present application, the bottom layer 506 may be of any other shape, like an elliptical shape, a triangular shape, or the like.

Furthermore, the dispense interface 500 comprises a first intermediate layer 516. The first intermediate layer 516 comprises substantially the same shape as the bottom layer 506. The first intermediate layer 516 comprises a first recess 522 and a second recess 524. As can be seen from FIG. 13, the first and second recesses 522, 524 are substantially linear. The first recess 522 is a linear recess 522 having a predefined length and width. The second recess 524 is a linear recess 524 having a predefined length and width. Preferably, the recesses 522, 524 are substantially equal and run in parallel to each other.

The first and second recesses 522, 524 can be formed by any suitable recessing technique, like a cutting technique, a stamping technique, an etching technique or the like.

The first recess 522 forms the first inlet channel 522 and second recess 524 forms the second inlet channel 524. Each of the first and second inlet channels 522, 524 comprises an inlet opening 526, 528. The first and the second proximal needle 512 and 514 can be inserted into the first and second inlet openings 526, 528.

In addition, the first intermediate layer 516 can be tightly connected with the bottom layer 506. On the top of the first intermediate layer 516, a third intermediate layer 520, which will be elucidated hereinafter, can be tightly attached. The consequence of the lamination of the three layers 506, 516, 520 is a first and a second hollow space, i.e. the first and second inlet channels 522, 524. A fluid can enter the first and second inlet channel 522, 524, respectively, via the first and second proximal needles 512, 514, respectively.

The third intermediate layer 520 comprises substantially the same shape as the bottom layer 506 and/or the first intermediate layer 516. The third intermediate layer 520 comprises a first opening 538 and a second opening 540. In the present example, the openings 538, 540 have a circular shape. It shall be understood that, according to other variants of the present application, the openings may differ from each other and/or may have another shape, like an elliptical shape, a triangular shape, a rectangular shape or the like.

The first and second opening 538, 540 can be formed by any suitable recessing technique, like a cutting technique, a stamping technique, an etching technique or the like.

The first opening 538 is configured for a fluid communication with the first inlet channel 522. In particular, the first opening 538 can be arranged at the end of the first inlet channel 522 which is opposite to the first inlet opening 526. The second opening 540 is configured for a fluid communication with the second inlet channel 524. In particular, the second opening 540 can be arranged at the end of the second inlet channel 524 which is opposite to the second inlet opening 528.

The first and second opening 538, 540 can be provided with a valve mechanism 542. The valve mechanism 542 may be a non return valve mechanism 542. For instance, the non return valve mechanism 542 may be thin polymer film which is laser cut forming a first and a second valve flap (not shown). The film 542 can be tightly attached to the third intermediate layer 520. Thereby, the non return valve mechanism 542 is configured such that if a pressure is exerted onto the laser cut film 542 from an inlet channel 522, 524, fluid can flow through the non return valve mechanism 542. If a pressure is exerted from the opposite direction, the non return valve mechanism 542 is kept close avoiding a fluid flow in the opposite direction.

Furthermore, the dispense interface 500 comprises a second intermediate layer 518. The second intermediate layer 518 comprises substantially the same shape as the previously described layers 506, 516, 520. The second intermediate layer 518 comprises a first linear recess 530. The first recess 530 forms the outlet channel 530. The outlet channel 530 comprises an outlet opening 532 for dispensing a fluid. The third needle 510, like the ejection needle 510, can be inserted into the outlet opening 532.

A second recess 534 is connected with the first recess 530 at the end of the first recess 530 wherein this end is opposite to the outlet opening 532. The second recess 534 forms a central space 534. A fluid communication between the central space 534 and outlet channel 530 is enabled.

Furthermore, the central space 534 can be arranged above the first and the second openings 538, 540 establishing a fluid communication between the first and second opening 538, 540 and the outlet channel 530.

The illustrated central space 534 comprises a substantially rectangular shape. It shall be understood that the central space 534 may be of any other shape as long as a fluid communication between the first and the second openings 538, 540 and the outlet channel 530 is possible.

The second intermediate layer 518 can be tightly connected to the third intermediate layer 520. On top of the second intermediate layer 518, the top layer 502 can be tightly attached. The consequence of the lamination of the three layers 502, 518, 520 is a first and a second hollow space, i.e. the central space 534 and the outlet channel 530. A fluid can enter the central space 534 via the first and/or second opening 538, 540 and can be dispensed via the outlet channel 530 and the third needle 510.

Preferably, all layers 502, 506, 516, 518, 520 are made of the (same) polymer material.

Figure 14:
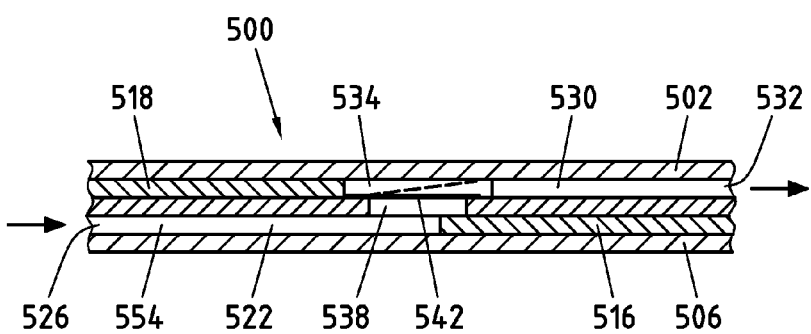
FIG. 14 illustrates a cross-sectional view of the dispense interface of FIG. 12.

FIG. 14 is a cross-sectional view of the dispense interface of FIG. 12. In particular, FIG. 14 illustrates the fluid flow through the dispense interface 500, in particular through the channel profile 554.

A fluid may enter the dispense interface 500 via the inlet opening 526. For instance, the fluid may enter the inlet channel 522 via a first proximal needle 512 (not shown in the present example). Then the fluid flows through the first inlet channel 522. Since a pressure is exerted onto the fluid, the fluid can pass the first opening 538 and in particular the non-return valve mechanism 542. The fluid can then flow via the central space 534 and the outlet channel 530 to the outlet opening 532. For instance, the fluid can be dispensed via an ejection needle 510 (not shown in the present example).

With regard to FIG. 14, it shall be noted that the cross sectional view is a simplified illustration and not a realistic representation of the dispense interface of FIG. 12. In particular, as can be seen from FIG. 13, normally, in a real cross sectional view either one inlet channel or the outlet channel should be visible, since the outlet channel does normally not lie within an axis of the first or second inlet channel. However, FIG. 14 has been introduced, since it illustrates the fluid flow through the dispense device in a demonstrative way.

Preferably, the design is fully symmetrical, so that the needles 510, 512, 514 are all inserted in a middle layer. This may be achieved by fluid channels that transfer the fluid flow first from the middle layer to a layer next to the middle layer. The construction with respect to the valve mechanism can then be designed as shown in FIGS. 13 and 14.

FIG. 15a to FIG. 15e illustrate different intermediates steps during the use of a dispense interface 500 according to the invention.

Figure 15A:
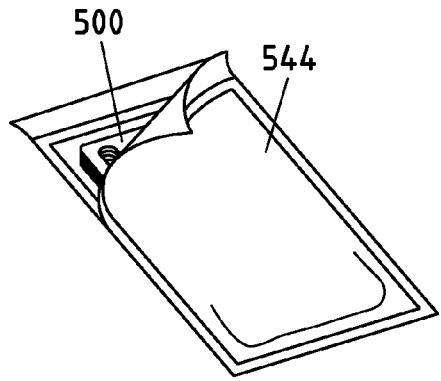
FIG. 15 illustrates different intermediates steps during the use of a dispense interface according to the invention.

In FIG. 15a, a packaging 544 comprising the dispense interface 500 is shown. The packaging 544 can be opened by a user and the dispense interface 500 can be removed from the packaging 544.

Figure 15B:
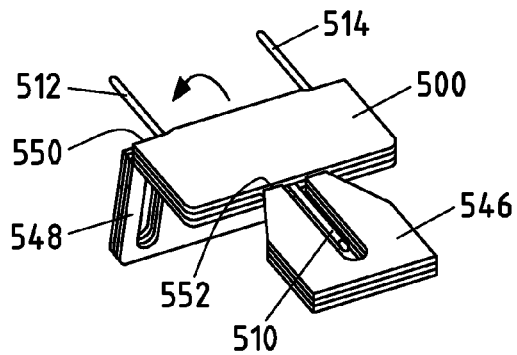

As can be seen from FIG. 15b, the dispense interface 500 is provided with a first safety element 548 and a second safety element 546. A safety element 546, 548 is configured to protect a user against injuries caused by the needles 510, 512, 514. Preferably, the first and second safety element 546, 548 are formed by an extension of the dispense interface 500. In particular, the first and second safety element 546, 548 comprises extensions of the plurality of layers.

A first predetermined breaking line 550 is provided between the first safety element 548 and the dispense interface 500. A second predetermined breaking line 552 is provided between the second safety element 546 and the dispense interface 500. A predetermined breaking line 550, 552 is configured for removing the respective safety element 546, 548 in a fast and simple manner. In the step shown in FIG. 15b, the first safety element 548 is removed.

Figure 15C:
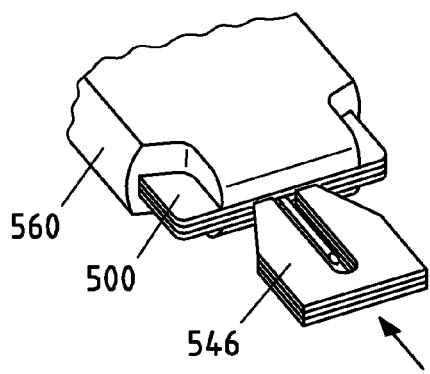
Figure 15D:
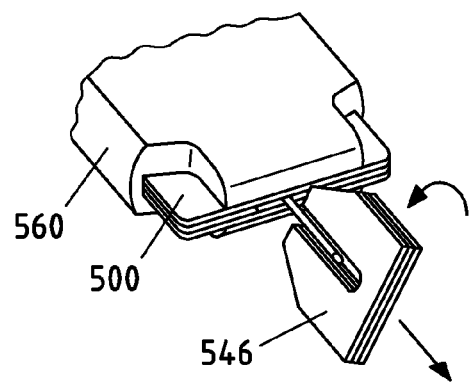
Figure 15E:
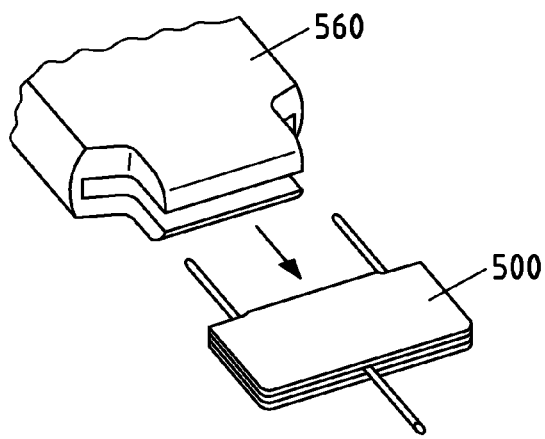

In FIG. 15c, the dispense interface 500 is attached to an ejection device 560, like a medical device. The ejection device comprises an intake corresponding to the dispense interface. Guiding elements can be arranged for simplifying the insertion of the dispense interface 500 into the ejection device 560. The first and second proximal needles 512, 514 can pierce corresponding reservoirs. A mechanism for ensuring a tight attachment can be provided.

In the next depicted step (FIG. 15d), the second safety element 546 can be removed from the third needle by a user. In particular, the second safety element 546 can be removed by a rotating and pulling movement.

After the ejection of at least one fluid of at least one reservoir, the dispense interface 500 can be detached from the ejection device 560 by e.g. a pulling movement. The dispense interface 500 can be disposed in a bin suitable for sharp devices while the packaging 544 can be disposed through the conventional household waste.

Figure 16:
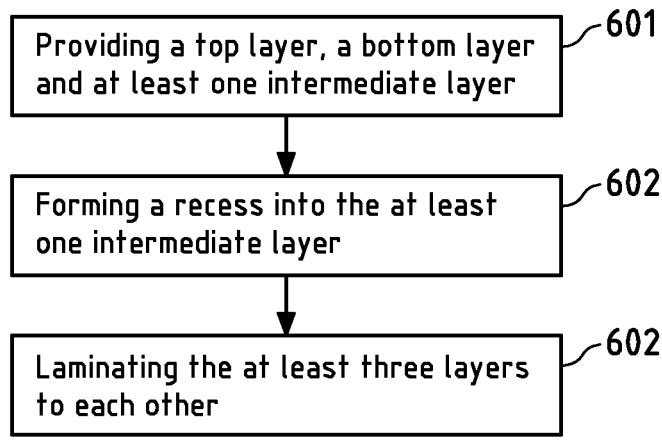
FIG. 16 illustrates a flowchart of a method according to the invention for manufacturing a dispense interface.

FIG. 16 illustrates a flowchart of a method according to the invention for manufacturing a dispense interface. In particular, the method can be used for manufacturing the previously described dispense interface.

In a first step 601, a top layer, a bottom layer and at least one intermediate layer can be provided. Preferably, all layers are made of a polymer material. It shall be understood that a plurality of intermediate layers can be provided.

In the following step 602, at least one recess can be formed into the at least one intermediate layer. The at least one recess forms at least one part of the channel profile. Preferably, a plurality of intermediate layers can be provided with recesses and/or openings for forming the channel profile of the dispense interface. For instance, the at least one recess can be cut out by a cutting device. For instance, a laser can be used. In alternative embodiments, the at least one recess can also be formed by stamping or etching techniques.

After forming the at least one recess, preferably all recesses, in an optional step, the inlet and outlet openings of the channel profile can be provided with needles. For instance, a first and second inlet opening can be provided with a first and second proximal needle, respectively. Furthermore, the outlet opening can be provided with a third needle, like an ejection needle.

In the next step 603, the at least three layers are tightly laminated to each other. In particular, adjacent layers can be laminated to each other, for instance, by bonding or welding. Preferably, the layers comprising the needles can be laminated to each other. In other words, also the needle can be tightly connected to the dispense device.

After the laminating step, in optional steps, the shape of the laminated layers can be changed by cutting or the like. Furthermore, if the dispense interface comprises at least one safety element, a predetermined breaking line can be provided between the safety element and the remaining component.

Figure 17:
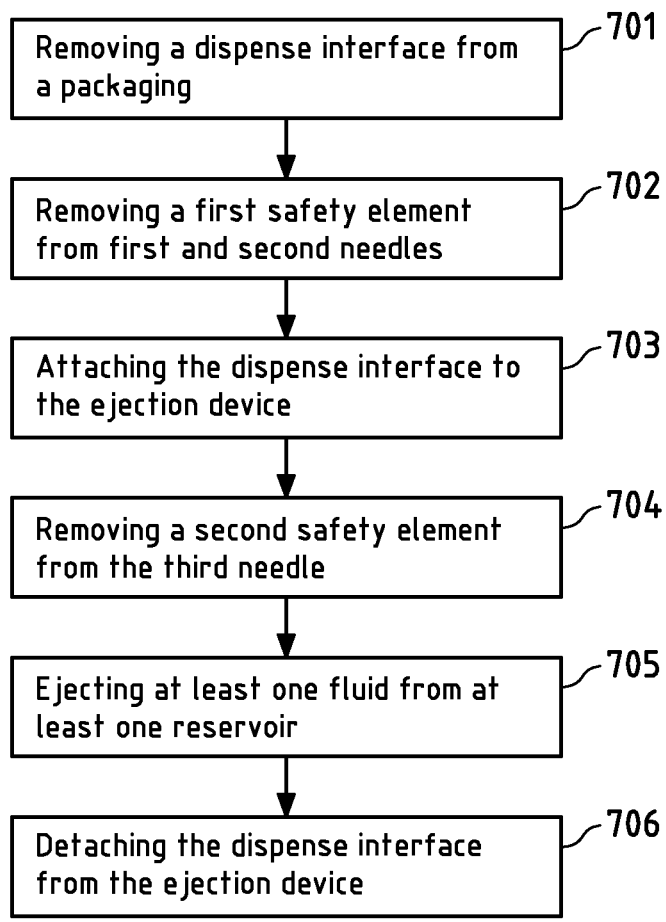
FIG. 17 illustrates a flowchart of a method according to the invention for using a dispense interface.

FIG. 17 illustrates a flowchart of a method according to the invention for using a dispense interface. In particular, the use of a previously described dispense interface is illustrated.

In a first step 701, a packaging of the dispense interface can be opened by a user and the dispense interface can be taken from the packaging.

Then, in step 702, if the dispense interface is provided with a first safety element, like a needle cover, the first safety element can be removed from the first proximal needle and/or the second proximal needle. For instance, if a predetermined braking line is provided, the first safety element can be detached by an angular movement performed by the user. It shall be understood that in alternative embodiments, the safety element can be formed by caps or the like.

After removing the first safety element, the first and second proximal needles are exposed. Then in step 703, the dispense interface is attached to an ejection device. In particular, the dispense interface is tightly attached to the ejection device. Thereby, the first proximal needle can puncture a first reservoir and the second proximal needle can puncture a second reservoir of the ejection device.

If the dispense interface comprises a second safety element for covering an ejection needle, in step 704, the second safety element is removed. The third needle, like an ejection needle, is exposed. The safety element can be an extension of the laminated layer structure of the dispense element. For instance, if a predetermined breaking line is provided, the safety element can be removed by a circular and pull movement performed by the user. For avoiding a detachment of the dispense interface from the ejection device, the predetermined breaking line can be first cut by the circular movement and then the safety element can be removed by a pull movement.

In the next step 705, at least one fluid of at least one reservoir can be ejected, as described hereinbefore. For instance, a drug or medicament can be ejected.

Afterwards, the used dispense interface is detached from the ejection device (step 706). For instance, the used dispense interface can be pulled out by the user.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39), wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(02)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp (02)25, Asp28] Exendin-4(1-39)-(Lys)6-NH2;
or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface comprising:
a channel profile with at least two inlet channels and at least one outlet channel,
wherein each of the at least two inlet channels is configured for fluid communication with a respective reservoir of at least two reservoirs,
at least one top layer and one bottom layer,
an intermediate layer structure arranged between the at least one top layer and one bottom layer,
wherein intermediate layer structure is tightly laminated with the top layer and the bottom layer,
wherein the intermediate layer structure comprises at least one intermediate layer comprising at least one recess for forming at least one part of the channel profile,
wherein the at least one intermediate layer comprises a first intermediate layer, wherein the at least one recess of the first intermediate layer comprises at least one first recess for forming at least one part of the first inlet channel and one second recess for forming at least one part of the second inlet channel, wherein the at least one intermediate layer comprises a second intermediate layer, wherein the at least one recess of the second intermediate layer comprises at least one first recess for forming at least one part of the outlet channel, and wherein the first intermediate layer is a flat layer comprising a presettable thickness and the second intermediate layer is a flat layer comprising a presettable thickness.

2. The dispense interface according to claim 1, wherein the second intermediate layer further comprises at least one second recess for forming at least one part of a central space configured for fluid connection between the outlet channel and the first inlet channel and the second inlet channel.

3. The dispense interface according to claim 2, wherein the at least one intermediate layer further comprises a third intermediate layer comprising at least a first opening configured for fluid connection between the first inlet channel and the central space and a second opening configured for fluid connection between the second inlet channel and the central space.

4. The dispense interface according to claim 3, wherein the at least two openings of the third intermediate layer are provided with a non return valve mechanism.

5. The dispense interface according to claim 4, wherein the non return valve mechanism is formed by a laser cut polymer film.

6. The dispense interface according to claim 1, wherein at least one of the plurality of layers is made of a polymer material.

7. The dispense interface according to claim 1,
wherein each of the at least two inlet channels comprises an inlet opening,
wherein the at least one outlet channel comprises an outlet opening, and
wherein at least one of the inlet or outlet openings is provided with a needle.

8. The dispense interface according to claim 1,
wherein at least one needle is covered with at least one safety element,
wherein the at least one safety element is formed by an extension of at least one of the plurality of layers.

9. The dispense interface according to claim 1, wherein a predetermined breaking line configured for removing the at least one safety element from the at least one needle is arranged.

10. A method for manufacturing a dispense interface comprising:
providing at least one bottom layer and one top layer,
providing an intermediate layer structure comprising at least one intermediate layer, wherein the at least one intermediate layer comprises a first intermediate layer and a second intermediate layer,
recessing at least the at least one intermediate layer for forming at least one part of a channel profile, such that the first intermediate layer comprises at least one first recess for forming at least one part of a first inlet channel and one second recess for forming at least one part of a second inlet channel and the second intermediate layer comprises at least one first recess for forming at least one part of an outlet channel,
tightly laminating the top layer and the bottom layer to the intermediate layer structure, and
wherein the first intermediate layer is a flat layer comprising a presettable thickness and the second intermediate layer is a flat layer comprising a presettable thickness.

11. A system comprising:
a dispense interface according to claim 1, and
an ejection device,
wherein the dispense interface is attached to the ejection interface.

12. The system according to claim 11, wherein the ejection device is a medical device for delivering at least two drug agents from at least two separate reservoirs.

* * * * *